(12) United States Patent
Antakly (10) Patent No.: US 10,702,488 B2
(45) Date of Patent: Jul. 7, 2020

(54) PPAR-γ ACTIVATORS, HDAC INHIBITORS AND THEIR THERAPEUTICAL USAGES

(71) Applicant: THERIAC BIOMEDICALE INC., Mont-Royal (CA)

(72) Inventor: Tony Antakly, Montreal (CA)

(73) Assignee: Theriac Biomedical Inc., Montreal, QC (CA)

( * ) Notice: Subject to any disclaimer, the term of this patent is extended or adjusted under 35 U.S.C. 154(b) by 0 days.

(21) Appl. No.: 16/226,436

(22) Filed: Dec. 19, 2018

(65) Prior Publication Data

US 2019/0298673 A1    Oct. 3, 2019

Related U.S. Application Data

(60) Provisional application No. 62/607,791, filed on Dec. 19, 2017.

(51) Int. Cl.

| | |
|---|---|
| A61K 31/192 | (2006.01) |
| A61K 31/235 | (2006.01) |
| A61K 31/167 | (2006.01) |
| A61K 38/12 | (2006.01) |
| A61K 31/427 | (2006.01) |
| A61K 38/15 | (2006.01) |
| A61K 31/4439 | (2006.01) |

(52) U.S. Cl.
CPC .......... *A61K 31/192* (2013.01); *A61K 31/167* (2013.01); *A61K 31/235* (2013.01); *A61K 31/427* (2013.01); *A61K 31/4439* (2013.01); *A61K 38/12* (2013.01); *A61K 38/15* (2013.01)

(58) Field of Classification Search
None
See application file for complete search history.

(56) References Cited

U.S. PATENT DOCUMENTS

| | | | |
|---|---|---|---|
| 7,998,971 B2 * | 8/2011 | Barlow | A61K 31/4355 514/292 |
| 2005/0124698 A1 * | 6/2005 | Kuo | C07C 59/68 514/571 |
| 2006/0247309 A1 * | 11/2006 | Hodge | A61K 31/192 514/541 |
| 2019/0292157 A1 * | 9/2019 | Casimiro-Garcia | C07D 403/12 |
| 2019/0298673 A1 * | 10/2019 | Antakly | A61K 38/15 |

FOREIGN PATENT DOCUMENTS

WO    WO 2012019295    *    2/2012

OTHER PUBLICATIONS

Ammonul (sodium phenylacetate and sodium benzoate Drug Insert Feb. 2005). (Year: 2005).*
Ichikawa etal (Fatal Hyperammonemiain a Patient with Systemic Lupus Erythematosus. Internal Medicine vol. 37, No. 8 (Aug. 1998)). (Year: 1998).*

(Continued)

*Primary Examiner* — Nancy Bitar (57) ABSTRACT

The invention relates to a composition for induction of activity of a nuclear receptor PPARγ and inhibition of HDAC in a subject in need thereof, which comprises a synergistic combination of benzoate and phenylbutyrate and/or phenylacetate in association with a pharmaceutical carrier.

7 Claims, 7 Drawing Sheets

(56) References Cited

OTHER PUBLICATIONS

Pharmacokinetics of sodium phenylacetate and sodium benzoate following intravenous administration as both a bolus and continuous infusion to healthy adult volunteers Robert B. MacArthur et al Dec. 2003 (Year: 2003).*

Investigator's Brochure of the FDA IND application # 140568 received Aug. 17, 2018. Author Tony Antakly. Sponsor: Theriac Biomedical Inc. Title; HIP-002. Powder for Oral Solution. Non-steroidal Anti-Inflammatory Drug (NSAID). (80 pages).

FDA IND application # 140568 Receipt Letter. Aug. 17, 2018. From Sponsor: Theriac Biomedical Inc. (7 pages).

* cited by examiner

PPAR-γ ACTIVATORS, HDAC INHIBITORS AND THEIR THERAPEUTICAL USAGES

BACKGROUND (a) Field

The subject matter disclosed generally relates to a novel composition of PPARγ activators including benzoate (BNZ) and phenylbutyrate (PBA) and/or phenylacetate, HDAC inhibitors and their therapeutic usages.

(b) Related Prior Art

Benzoate (BNZ) and phenylbutyrate (PBA) were individually studied for possible bioactivities in reducing inflammation, cancer growth and alleviating symptoms in animal models of experimental neurological disorders, namely multiple sclerosis, ALS, Huntington's disease and encephalopathy.

The clinical use of BZN and phenylacetate (PAA) in lowering plasma ammonium levels in patients with lethal hyperammonemia was established (1, 2). In certain metabolic diseases resulting from defects in urea cycle enzymes, ammonium, which cannot be converted to urea, accumulates to a toxic level that can be lethal. A drug combination of PAA and BNZ is particularly useful to treat patients with congenital errors of metabolism of the urea cycle enzyme, thus preventing complications such as encephalopathy (1, 2). In fact, PAA, through mitochondrial conjugation with glutamine, results in the formation of phenylacetylglutamine compound. Similarly, BNZ combines with glycine forming benzoylglycine (hippuric acid). These two non-toxic compounds, phenylacetyglutamine and benzoylglycine are easily eliminated in the urine. Enns et al. (2) reported the results of a 25-year clinical study, using a drug consisting of a combination of PAA and BNZ, to treat patients with urea cycle disorders, demonstrating an overall survival rate of 84%.

PAA and phenylbutyrate (PBA) both display important bioactivities other than those cited above. Chemically, PAA and PBA belong to a group of aromatic fatty acids having a stable phenyl ring. These compounds were proven useful in the treatment of several diseases, including, sickle cell anemia (3), amyotrophic lateral sclerosis (4), Huntington's disease (5), neuronal inflammatory conditions (6) and cancer (7). Initially, PAA was discovered as a plant hormone that regulates cell growth (8). It has been extensively studied in the past two decades as an anti-cancer agent and cellular differentiating compound in laboratory settings and clinical trials. In fact, PAA inhibits the growth of several cancer cell types of different lineages and, in some instances, it promotes their differentiation to a non-cancerous phenotype. Of interest are the effects of PAA and PBA on gliomas and neuroblastomas, originally thought to be mediated by the inhibition of protein prenylation as well as cholesterol and fatty acid biosynthesis (5). Studies have demonstrated that PAA and PBA inhibit the growth of several neoplastic cell types, including breast cancer, prostate cancer, colon cancer and thyroid carcinoma. These anti-cancer actions of PAA and PBA have prompted the initiation of several clinical trials since these compounds display little toxicity if any (4, 5, 7).

The exact mechanisms underlying these physiological and pharmacological effects of BNZ, PAA and its butyrate metabolites are not completely known, but regulatory effects of butyrate derivatives have involved inhibition of histone deacetylation, which modulates chromatin conformation and regulation of nuclear receptor gene expression (9).

The present applicant PCT co-pending application published under No. WO2017/091895 in the name of Theriac Biomedicale Inc. discloses a composition for induction of activity of a nuclear receptor PPARγ in a subject in need thereof, which comprises at least one of benzoate or a synergistic combination of benzoate and phenylacetate in association with a pharmaceutical carrier. There is no disclosure or suggestion of a composition comprising PBA and BZA in this co-pending application.

The pharmacokinetic known effects of PBA and PAA are so different that these compounds are not used interchangeably. More precisely, PBA is a more effective anti-cancer and a more potent antitumor agent than PAA: PBA is effective against cervical cancer cells whereas PAA is not; PBA is more effective than PAA against breast cancer cells and malignant B cells.

However to date, PBA and BNZ were never combined to show a synergistic effect as activators of PPARγ.

SUMMARY

According to an embodiment, there is provided A pharmaceutical composition to improve disease symptoms by induction of activity of a nuclear receptor PPARγ and inhibition of HDAC in a subject in need thereof, which comprises a synergistic combination of a PPARγ activator and a HDAC inhibitor in association with a pharmaceutical carrier.

The PPARγ activator is selected from the group consisting of phenylbutyrate, phenylacetate, benzoate, Troglitazone, rosiglitazone, and pioglitazone; and the HDAC inhibitor is selected from the group consisting of phenylbutyrate, phenylacetate, trichostatin-A, Vorinostat, romidepsin, valproate, and apicidin.

Preferably, benzoate may be present between 10 to 250 mg/kg and phenylbutyrate and/or phenylacetate is present between 0.1 to 1000 mg/kg.

Most preferably, benzoate is present at a dosage of 50 to 100 mg/kg and phenylbutyrate and/or phenylacetate is present at a dosage of 4 to 25 mg/kg.

There is also provided a method of treatment, wherein the induction of activity of a nuclear receptor PPARγ improves symptoms of at least one of Inflammation and pain (osteoarthritis, rheumatoid arthritis), pain, autoimmune diseases (Lupus erythematous), neurodegenerative inflammatory diseases (Multiple Sclerosis, Parkinson disease, Alzheimer, ALS, Huntington), anti-cancer, diabetes type 2, to replace PPARγ agonists in other metabolic diseases.

According to another embodiment, there is provided use of a synergistic combination of benzoate and phenylacetate in association with a pharmaceutical carrier for inducing activity of a nuclear receptor PPARγ in a subject in need thereof.

The use of this combination, wherein the inducing activity of a nuclear receptor PPARγ improves symptoms of at least one of inflammation and pain (osteoarthritis, rheumatoid arthritis), psoriatic arthritis, juvenile arthritis, ankylosing spondylitis, gout, pain, autoimmune diseases (Lupus erythematous), neurodegenerative inflammatory diseases (Multiple Sclerosis, Parkingson disease, Alzheimer, ALS, Huntington), anti-cancer, diabetes type 2, to replace PPARγ agonists in other metabolic diseases.

According to another embodiment, there is provided a method of inducing activity of a nuclear receptor PPARγ in a subject in need thereof, which comprises administering to the subject a synergistic combination of benzoate and phenylacetate in association with a pharmaceutical carrier.

The inducing activity of a nuclear receptor PPARγ improves symptoms of at least one of Inflammation and pain (osteoarthritis, rheumatoid arthritis), psoriatic arthritis, juvenile arthritis, ankylosing spondylitis, gout, pain, autoimmune diseases (Lupus erythematous), neurodegenerative inflammatory diseases (Multiple Sclerosis, Parkinson disease, Alzheimer, ALS, Huntington), anti-cancer, diabetes type 2, to replace PPARγ agonists in other metabolic diseases.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which:

FIGS. 2A-2F illustrate histology examples of carrageenan-induced leukocyte tissue infiltration. Acute paw inflammation was induced by intraplantar carrageenan injection. Tissue leukocyte infiltration was evaluated 4-hours post carrageenan injection in hematoxylin-eosin stained paw tissue sections. Photos are representative of a placebo mouse injected with 0.9% NaCl (FIGS. 2A-2B), a positive control mouse injected with 3 mg/kg indomethacin (FIGS. 2C-2D) and a mouse treated with HIP-002 (FIGS. 2E-2F) consisting of a mixture of 100 mg/kg sodium benzoate and 10 mg/kg sodium phenylbutyrate. All treatments were administered i.p. 90 min after carrageenan. In addition to the i.p. injection, HIP-002 was also given by intraplantar injection concomitantly with carrageenan. The same areas outlined in FIGS. 2A, 2C and 2E are shown at higher magnification, respectively, in FIGS. 2B, 2D and 2F. Bars=100 μm.

FIG. 3A illustrates treatment reduces carrageenan-induced leukocyte infiltration. Legend: Acute inflammation was induced by intraplantar carrageenan injection into the right hind paw. Tissue leukocyte infiltration was quantified under the microscope by an expert hematologist blinded to treatment conditions. Hematoxylin-eosin stained paw tissue sections were evaluated at 4-hours post carrageenan injection. Placebo group received 0.9% NaCl solution, the positive control group received indomethacin (3 mg/kg i.p.). The other tested groups as shown, were a combination of benzoate 100 mg/kg of benzoate (BZN) and 10 mg/kg of either PBA or PAA. Total leukocytes (white blood cells) per tissue area were quantified. All data are presented as mean±SEM. P values versus placebo in one-way ANOVA followed by Holm-Sidak are depicted on the graph by (**) indicating p<0.01. Number of mice per group is 5.

FIG. 3B illustrates HIP-002 reduces carrageenan-induced paw edema. Acute inflammation was induced by intraplantar carrageenan injection into the right hind paw. Paw edema was determined by measuring paw volume before and 4-hours after carrageenan injection. Ninety minutes after carrageenan the placebo control group received 0.9% NaCl solution (i.p.) and the positive control group received indomethacin (3 mg/kg i.p.). Treatments were given by intraplantar injection (together with carrageenan) and by i.p. injection (90 min after carrageenan). BZN+PBA doses were 100 mg/kg BZN and 0.10 mg/kg of PBA 100/10. The far right group received BZN 100 mg/kg and PAA 10 mg/kg. All data are presented as mean±SEM. (*) P<0.05 versus placebo in one-way ANOVA followed by Holm-Sidak. Number of mice per group is 10.

FIG. 4A illustrates the effects of HIP-002 on in vitro assays of PPARγ and HDAC activities. Human embryonic kidney (HEK) 293 cells were transfected with a luciferase reporter gene construct under the control of a Gal4-DNA binding upstream-activating sequence (UAStkLuc) in the presence of an expression plasmid encoding Gal4 DNA-binding domain fusion to human PPARγ. In this assay, luciferase activity is a direct measurement of PPARγ activation.

FIG. 4B illustrates the effects of HIP-002 on in vitro assays of PPARγ and HDAC activities. The detection of HDAC activity is based on a two-step enzymatic reaction. i.e., deacetylation of a lysine residue bound to a fluorescent group, followed by the cleavage of the deacetylated substrate and release of the free, highly fluorescent group. The measured fluorescence is directly proportional to the deacetylation activity of the sample. Data represent HDAC activity in response to increasing concentrations of HIP-002. Curves were fitted using a three-parameter non-linear fit (inhibitor-response) in GraphPad Prism 7.02.

DETAILED DESCRIPTION

The combination of benzoate and phenylbutyrate and/or phenylacetate induces the activity of the nuclear receptor PPARγ. This transcription factor is a member of the steroid receptor superfamily and master regulator of lipid metabolism, inflammation and a key target for insulin-regulating drugs.

Furthermore, the usefulness of concomitant treatment of benzoate and phenylbutyrate and/or phenylacetate in the treatment of osteoarthritis is demonstrated in a rodent model of osteoarthritis.

The present invention will be more readily understood by referring to the following examples which are given to illustrate the invention rather than to limit its scope.

Example 1

Indications for the Mixture of PBA/PAA & BZN in Humans and Animals

Inflammation and pain including but not limited to osteoarthritis, rheumatoid arthritis, atherosclerosis, periodontitis, hay fever
Psoriatic arthritis
Juvenile arthritis
Ankylosing spondylitis
Gout
Pain
Autoimmune diseases including but not limited to Addison's disease, Agammaglobulinemia, Alopecia areata, Amyloidosis, Ankylosing spondylitis, Anti-GBM/Anti-TBM nephritis, Antiphospholipid syndrome (APS), Autoimmune hepatitis, Autoimmune inner ear disease (AIED), Axonal & neuronal neuropathy (AMAN), Behcet's disease, Bullous pemphigoid, Castleman disease (CD), Celiac disease, Chagas disease, Chronic inflammatory demyelinating polyneuropathy (CIDP), Chronic recurrent multifocal osteomyelitis (CRMO), Churg-Strauss, Cicatricial pemphigoid/benign mucosal pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Discoid lupus, Dressler's syndrome, Endometriosis, Eosinophilic esophagitis (EoE), Eosinophilic fasciitis, Erythema nodosum, Essential mixed cryoglobulinemia, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis, Graves' disease, Guillain-Barre syndrome, Hashimoto's thyroiditis, Hemolytic anemia, Henoch-Schonlein purpura (HSP), Herpes gestationis or pemphigoid gestationis (PG), Hypogammalglobulinemia, Huntington disease, IgA Nephropathy, IgG4-related sclerosing disease, Inclusion body myositis (IBM), Interstitial cystitis (IC), Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus, Lupus erythematous, Lyme disease chronic, Meniere's disease, Microscopic polyangiitis (MPA), Mixed connective tissue disease (MCTD), Mooren's ulcer, Mucha-Habermann disease, Multiple sclerosis (MS), Myasthenia gravis, Myositis, Narcolepsy, Neuromyelitis optica, Neutropenia, Ocular cicatricial pemphigoid, Optic neuritis, Palindromic rheumatism (PR), PANDAS (Pediatric Autoimmune Neuropsychiatric Disorders Associated with *Streptococcus*), Paraneoplastic cerebellar degeneration (PCD), Paroxysmal nocturnal hemoglobinuria (PNH), Parry Romberg syndrome, Pars planitis (peripheral uveitis), Parsonnage-Turner syndrome, Pemphigus, Peripheral neuropathy, Perivenous encephalomyelitis, Pernicious anemia (PA), POEMS syndrome (polyneuropathy, organomegaly, endocrinopathy, monoclonal gammopathy, skin changes), Polyarteritis nodosa, Polymyalgia rheumatica, Polymyositis, Postmyocardial infarction syndrome, Postpericardiotomy syndrome, Primary biliary cirrhosis, Primary sclerosing cholangitis, Progesterone dermatitis, Psoriasis, Psoriatic arthritis, Pure red cell aplasia (PRCA), Pyoderma gangrenosum, Raynaud's phenomenon, Reactive Arthritis, Reflex sympathetic dystrophy, Reiter's syndrome, Relapsing polychondritis, Restless legs syndrome (RLS), Retroperitoneal fibrosis, Rheumatic fever, Rheumatoid arthritis (RA), Sarcoidosis, Schmidt syndrome, Scleritis, Scleroderma, Sjogren's syndrome, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis, Thrombocytopenic purpura (TTP), Tolosa-Hunt syndrome (THS), Transverse myelitis, Type 1 diabetes, Ulcerative colitis (UC), Undifferentiated connective tissue disease (UCTD), Uveitis, Vasculitis, Vitiligo, Wegener's granulomatosis (now termed Granulomatosis with Polyangiitis (GPA)

Neurodegenerative inflammatory diseases including but not limited to Multiple Sclerosis, Parkinson disease, Alzheimer, ALS or Lou Gehrig's disease, Huntington Cancer Diabetes type 2

To Replace PPAR gamma agonists in other metabolic diseases

To regulate gene expression by boosting histone deacetylase inhibition.

Example 2

Anti-Inflammatory Actions of PBA and/or PAA in Combination with BZN

To test such a hypothesis, the anti-inflammatory effects of combined BZN and PBA and/or PAA were assessed in two inflammation models: a mouse model of carrageenan-induced acute inflammation (Morris C J., *Methods Mol Biol* 2003; 225:115-21) and a rat model of osteoarthritis (OA) (Bove S E et al. *Osteoarthritis Cartilage* 2006; 14(10): 1041-8).

These models were selected because they are well-established, reliable and reproducible rodent models that allow the evaluation of pain and inflammation. Briefly, in the carrageenan-induced acute inflammation model (Morris 2003), a rapid inflammatory response is triggered by the injection of a small volume of a solution containing carrageenan in the paw of adult mice. Paw edema, tissue leukocyte infiltration and tactile allodynia usually develop within few minutes and last several hours. After induction of the lesion (carrageenan or OA), animals were tested for drug response. All experiments included a placebo group injected with physiological NaCl 0.9% solution, a positive control group receiving indomethacin (carrageenan-model) or pregabalin+ carprofen (in the OA model) and one or more group receiving test doses of HIP-002 (a composition consisting of a mixture of PBA+BZN or PAA+BZN).

Drugs for the positive control groups were chosen with the following rationale: Indomethacin is a fast-acting non-steroidal anti-inflammatory drug (NSAID) commonly used to treat inflammation and was used at its minimally effective dose. The dose range of HIP-002 was selected based on the effective concentration (EC50) obtained with experiments in vitro or in vivo pilot experiments.

Different experiments were used to evaluate diverse aspects of inflammation:
  a. measurements of paw edema and leukocyte tissue infiltration were done in the carrageenan test to assess acute inflammation.

Results

Carrageenan-Induced Acute Inflammation

In this study (UOM-01-R1-Carr), acute inflammation was induced in Swiss mice by intraplantar (i. plant.) injection of 20 µL 1% carrageenan (N=10 or 11 mice per group). Ninety minutes after carrageenan, mice were treated with either placebo (0.9% NaCl solution), indomethacin (3 mg/kg) or our test drug, code named HIP-002 whose concentration were (100+10 mg/kg of BZN+PBA respectively). In one group, PAA was used instead of PBA.

Figure 1:
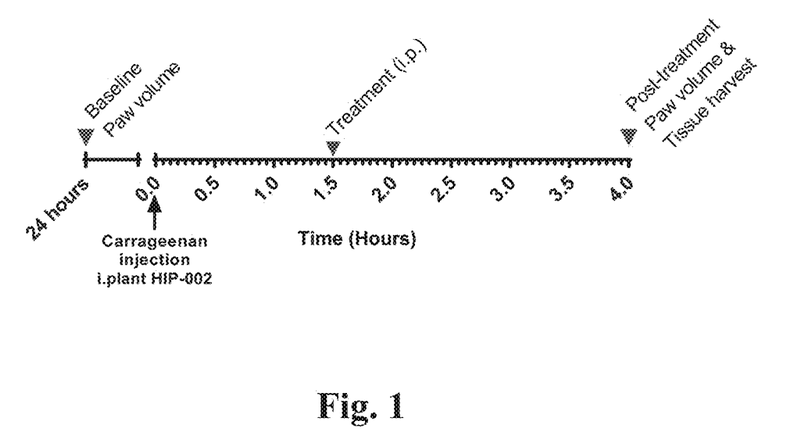
FIG. 1 illustrates the time-course of carrageenan-induced acute inflammation study design.
Figure 2A:
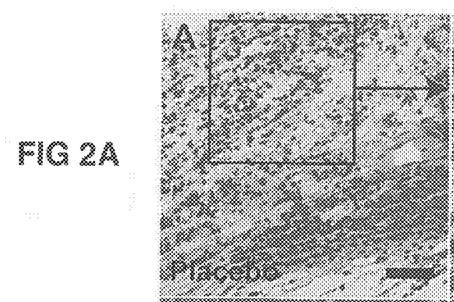
Figure 2B:
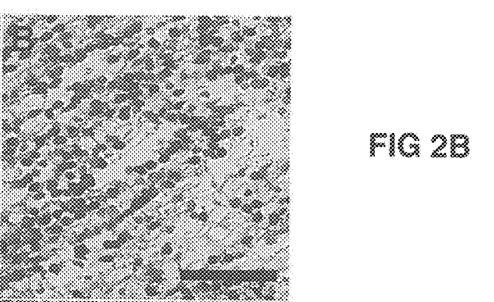
Figure 2C:
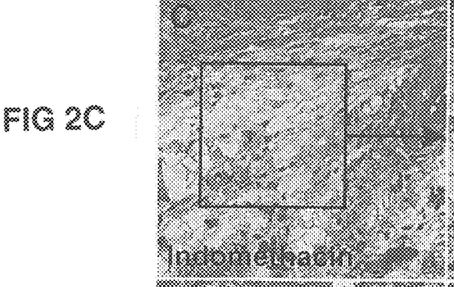
Figure 2D:
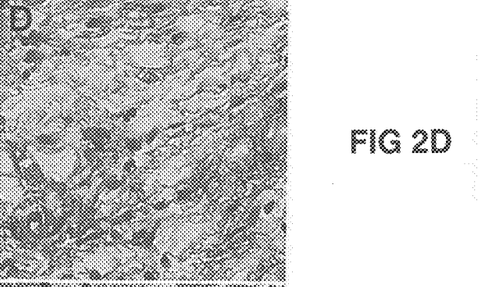
Figure 2E:
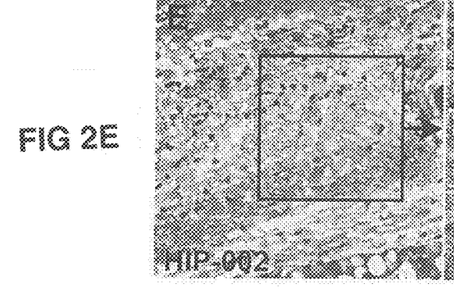
Figure 2F:
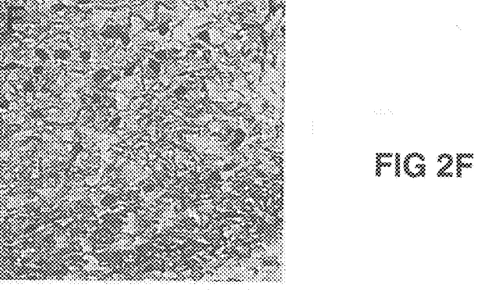
Figure 3A:
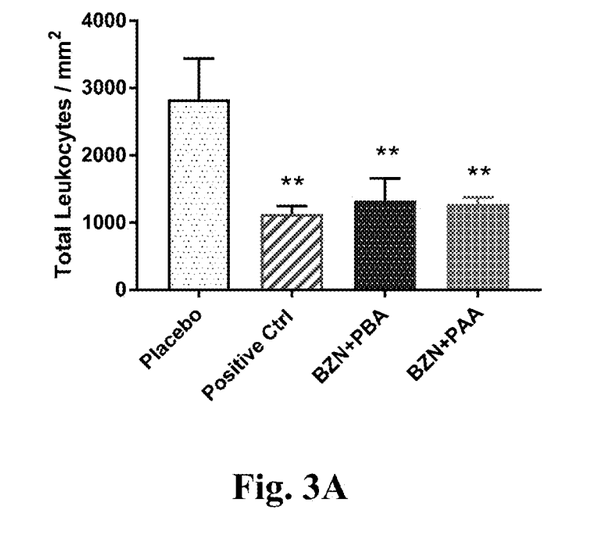
Figure 3B:
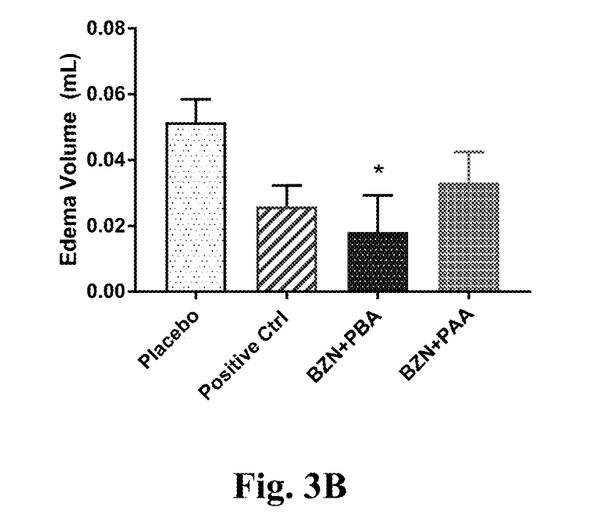

Test articles, including placebo, were also injected intraplantarly (10 µL) at the same time of carrageenan. The study schedule assessment is depicted in FIG. 1, doses, route and results are summarized in Table 1 below.

TABLE 1

Summary of effects of HIP-002 on Carrageenan-Induced Acute Inflammation

| Experiment | Doses and Administration Route of (BZN + PBA) and BZN + PAA | Tests | Method of Analysis | Noteworthy Observations |
|---|---|---|---|---|
| Carrageenan-induced acute inflammation Swiss mouse (10 or 11 mice/group) | Groups Description: saline i.p.: 1 mL/kg i.plant. 10 µL 100 BZN + either PBA or PAA 10 mg/kg i.p. and i.plant. indomethacin i.p.: 3 mg/kg i.plant. 0 µg | Leukocyte Tissue infiltration Immune cell migration Paw edema Swelling response | Quantification of infiltrated immune cells in H-E stained histology sections of paws Paw volume measured in a plethysmometer | Reduced number of immune cells in the paw of positive control groups BZN + PBA ↓ leukocyte infiltration Reduced carrageenan-induced edema in BZN + PBA treated group when compared to placebo. ↓ paw swelling |

As part of its biological action, PBA and PAA is known to be a histone deacetylase inhibitor (HDACi). The HDACi action induces conformational changes in chromatin, thereby regulating the overall gene expression of target cells (Nor et al. *Mol Neurobiol* 2013, 48(3):533-543). We discovered that by combining benzoate compounds with PBA and/or PAA, the HDACi activity is enhanced as compared to placebo or appropriate positive control. We tested HIP-002 or PBA alone for HDACi in vitro using normal, primary cultured (chondrocytes, osteoblasts) and cancer cell lines (breast cancer, prostate, bladder, and glioblastoma) at concentrations ranging from 1-10 mM. As positive control, trichostatin-A, a known HDACi, was used (at 100-500 nM doses). We also tested for HDACi, the paw tissue extract homogenates (prepared from the carrageenan or OA rodent experiments described elsewhere in this patent application). The HDACi activity was measured using a classic assay method (such as described by Sigma-Aldrich case # CS1010). We found that the combination of PBA (or PAA) with BZN is significantly more potent than PBA alone. Furthermore, PBA alone or in combination is more potent than PAA.

To test either the effect of HDAC inhibition by PBA (or PAA) or the stimulation of PPAR γ, we tested HIP-002 to induce PPARγ transcriptional activity using a cellular one-hybrid luciferase reporter gene assay as previously described (Avalone et al, 2006 *Mol. Endocrinol.* 20(12):3165-3178). Human embryonic kidney 293 cells were transfected with a luciferase reporter gene construct under the control of a Gal4-DNA binding upstream-activating sequence (UAStk-Luc) in the presence of an expression plasmid encoding Gal4 DNA-binding domain fusion to human PPARγ. A significant and dose-dependent increase in PPARγ activity was observed upon administration of HIP-002

Figure 4:
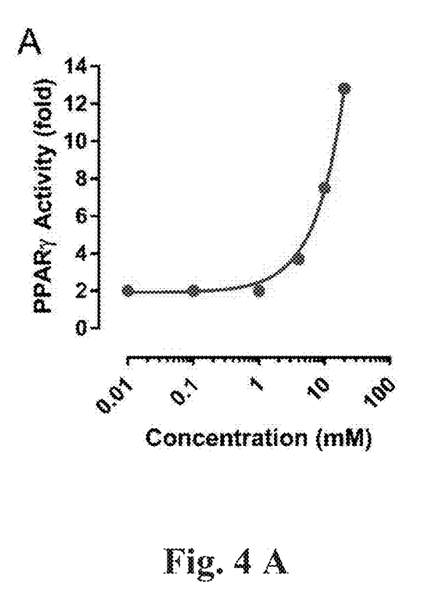

Results are illustrated in FIG. 4.

Example 3

Pathology Test

The overall objective of the study was to compare the efficacy of the test item, Compound HIP-002, following either a surgically induced osteoarthritis in female Sprague-Dawley rats and further to compare the withdrawal thresholds using the Von Frey and Paw Withdrawal tests.

The specific objective of the Pathology sub-study was to examine the histopathological differences between the experimental groups, particularly with respect to the extent of inflammation and cytology of the hyaline layer and other cells of the knee joint.

Experimental Design

The test item, Molecule HIP-002 is described in this application. The positive control comprises of Pregabalin and Carprofen. The placebo (control) item was 0.9% Physiological saline USP.

The test, positive, and placebo (control)/vehicle items were administered to groups of rats daily as follows by oral (Gavage) and Carprofen was administered by subcutaneous (SC) injection (administration was one after the other). Administration was for a duration of 39 or 40 consecutive days as described.

Animals were euthanized either on Day 40 or 41 upon completion of the dosing periods and following an overnight period without food. These animals were anesthetized with Isoflurane followed by exsanguination. Gross pathology consisted of an external examination, including identification of all clinically-recorded lesions, as well as a detailed internal examination. Pre-treatment conditioned knee samples were retained from all animals, processed according to the study plan and examined histopathologically.

Results and Discussion

Mortality

There were no macro or microscopic findings that could be confirmed to be test item-related. Dark discoloration of the mandibular and mediastinal lymph nodes was regarded as procedure-related finding. There were no other findings seen at necropsy of this female.

Microscopically, mild diffuse chronic inflammation of the joint capsule and mild granular basophilic material with cell debris/eosinophilic material in the joint cavity was observed and considered to be caused by the pre-treatment procedure. These findings confirmed that the pre-treatment procedure was able to cause inflammatory changes in the joint.

Macroscopic Findings

Crust on the right knee was seen in one Group 1 animal. All other findings were considered to be incidental or procedure-related.

Microscopic Findings

In general, the same findings of the right knee consisting of diffuse chronic inflammation of the joint capsule and granular basophilic material in the joint cavity were observed in both group designations but with a higher incidence and severity of these findings in the knee injection osteoarthritic-induced method designated groups, when compared with the surgical osteoarthritic-induced method designated groups.

Minimal to mild diffuse chronic inflammation of the joint capsule and minimal granular basophilic material with cell debris/eosinophilic material in the joint cavity were observed in the animals of all three groups where osteoarthritis was induced by surgical method.

The highest severity of the findings was seen in Placebo (Control) group, where no positive treatment and/or treatment by HIP-002 was performed. Severity of the diffuse chronic inflammation was lower in the Molecule HIP-002 group (7 minimal and 3 mild) when compared with Positive Control group (4 minimal and 6 mild) and Placebo Control group (3 minimal and 7 mild).

Minimal to moderate diffuse chronic inflammation of the joint capsule and minimal to mild granular basophilic material with or without cell debrisleosinophilic material in the joint cavity were observed in animals of both groups where osteoarthritis was induced. While the incidence and severity of the granular basophilic material in the joint cavity was comparable in both groups, severity of diffuse chronic inflammation of the joint capsule was slightly decreased in the group treated by HIP-002 when compared with the Placebo Control group.

Conclusion

Administration of HIP-002 after induced osteoarthritis (section through the cruciate ligament and tear of medial meniscus) or after iodoacetate knee injection was associated with a lower incidence of diffuse chronic inflammation of the joint capsule, when compared with Positive Control animals treated with Pregabalin (orally) and Carprofen (subcutaneously) and with untreated animals (Placebo Control).

Furthermore, HIP-002 administration was associated with a lower incidence of diffuse chronic inflammation of the joint capsule, when compared with untreated animals (Placebo Control).

Histopathology:

At day 36 animals were sacrificed and had the right knee dissected, imbedded in paraffin and sectioned for histopathology. Histological sections were stained with safranin-O, a special histochemical stain for visualization of cartilage.

Figure 5:
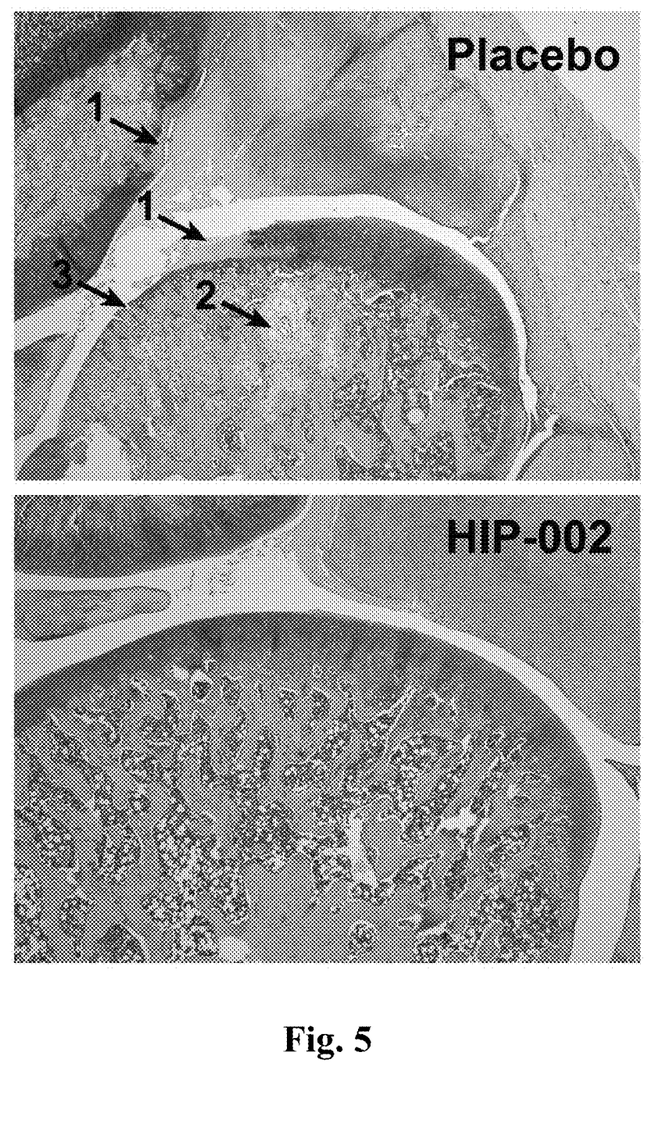
FIG. 5 illustrates An example of Histopathology in Placebo and HIP-002 Treated Rats.

In FIG. 5 histological sections were stained with safranin-O, a special histochemical stain for visualization of cartilage (tissue in red). Sections were obtained after surgical induction of osteoarthritis followed by treatment with placebo (top) or HIP-002 (bottom). Note damaged cartilage at tibia/ femur interface in placebo treated rat, unlike the HIP-002 treated one. Also, note differences in bone eburnation and bone marrow fibrosis. 1: cartilage damage, 2: Fibrosis in bone marrow, 3: bone eburnation, 4: preserved cartilage, 5: preserved bone.

Figure 6:
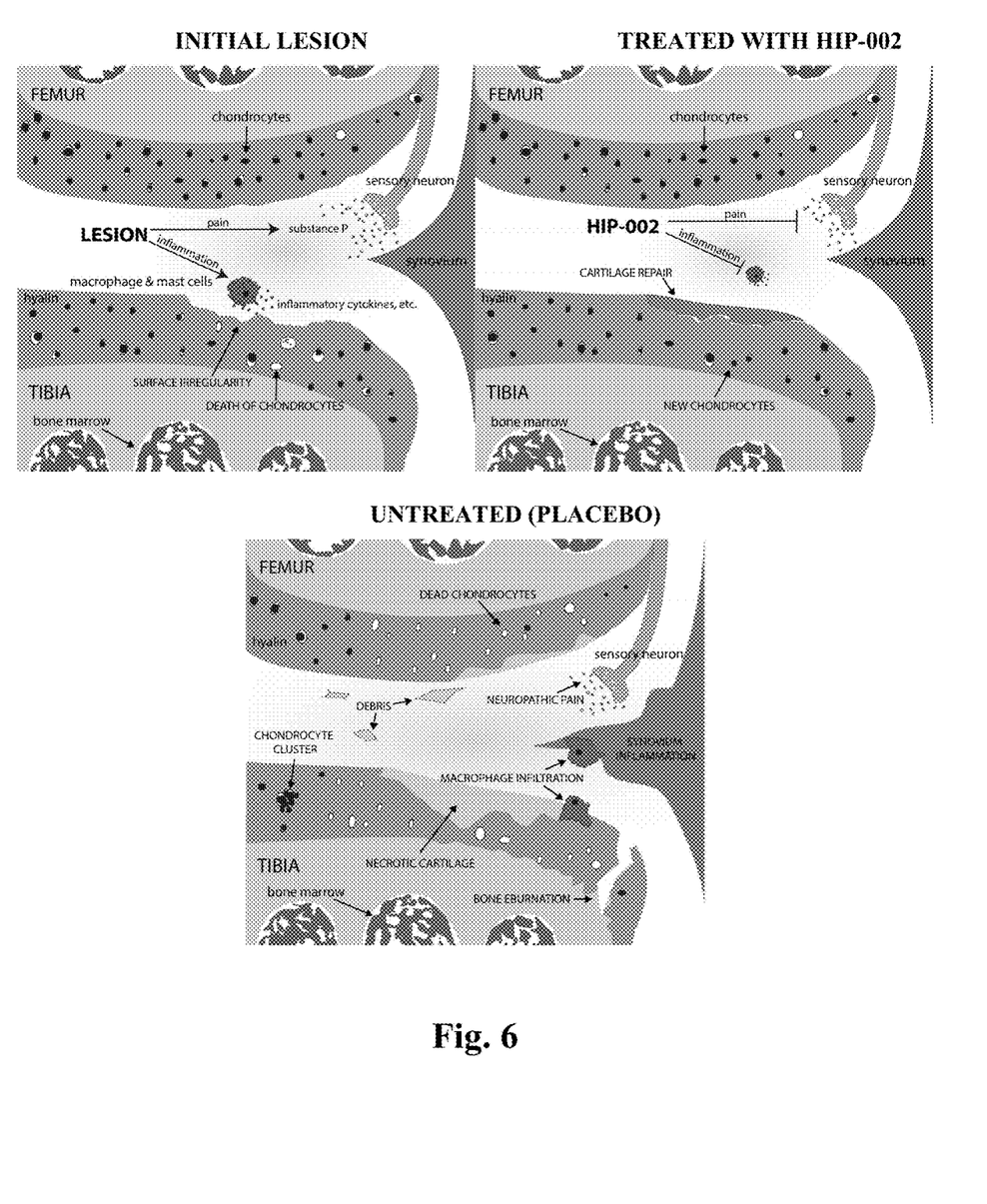
FIG. 6 illustrates the proposed mechanism of action for HIP-002 in the OA knee based on pre-clinical data.

In FIG. 6 After induction of OA by an initial lesion (top left panel), inflammatory cytokines and substance P are released, respectively, by immune cells and sensory neurons, to mediate inflammation and pain. HIP-002 acts by reducing cytokines and substance P levels, thus preventing further damage caused by chronic inflammation of the injury. Following treatment with HIP-002 (top right panel) inflammation and pain are reduced and the cartilage layer is repaired. An untreated lesion (bottom panel), however, leads to inflamed and infiltrated synovium, necrotic cartilage, death of chondrocytes, development of neuropathic pain and severe impairment of the articulation.

Proposed Molecular Mechanism of Action

The exact mechanisms underlying the physiological and pharmacological effects of sodium benzoate (BZN), and phenylbutyrate (PBA) and/or phenylacetylate (PAA) is shown below. The key feature suggests a direct inhibition on HDAC (like other histone modifying agents) and activation PPARγ gene regulation (in a manner similar to steroidal hormones).

Figure 7:
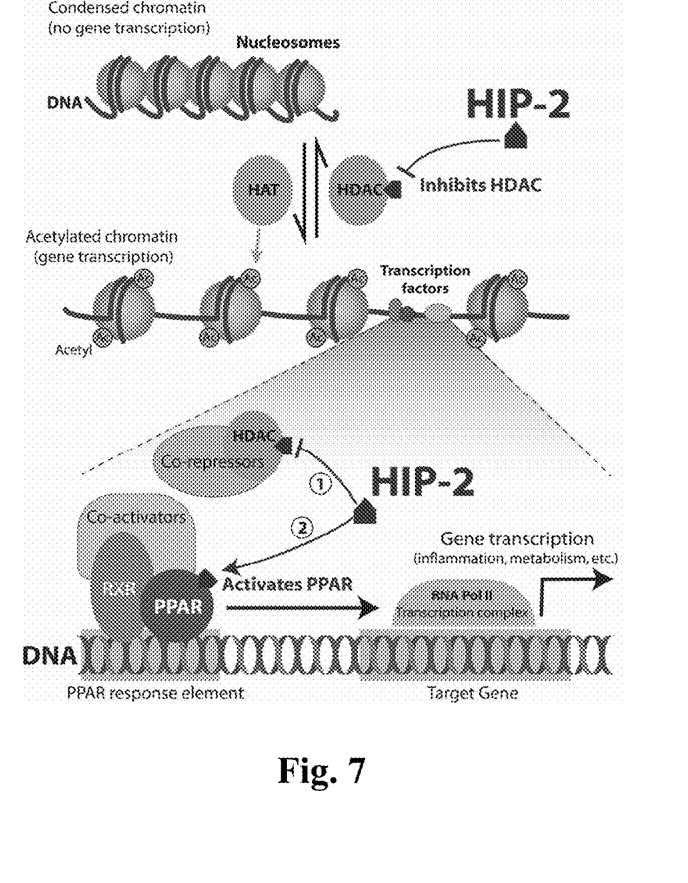
FIG. 7 illustrates proposed molecular mechanism of HIP-002 action at the genomic level.

In FIG. 7 HIP-002 is made of two molecules, which target two separate but complementary pathways in the cell nucleus. (1) inhibits Histone Deacetylase (HDAC), thereby regulating chromatin remodeling; and (2) activate PPAR, resulting in interaction of PPARγ with the transcription complex and allowing expression of key cellular proteins that ultimately modulate physiological responses.

While preferred embodiments have been described above and illustrated in the accompanying drawings, it will be evident to those skilled in the art that modifications may be made without departing from this disclosure. Such modifications are considered as possible variants comprised in the scope of the disclosure.

REFERENCE LIST

1. Brusilow S W, et al. (1984) Treatment of episodic hyperammonemia in children with inborn errors of urea synthesis. *N. Engl. J. Med.* 310(25):1630-1634.
2. Enns G M, et a. (2007) Survival after treatment with phenylacetate and benzoate for urea-cycle disorders. *N. Engl. J. Med.* 356(22):2282-2292.
3. Resar L M, et a. (2002) Induction of fetal hemoglobin synthesis in children with sickle cell anemia on low-dose oral sodium phenylbutyrate therapy. *J. Pediatr. Hematol. Oncol.* 24(9):737-741.
4. Cudkowicz M E, et al. (2009) Phase 2 study of sodium phenylbutyrate in ALS. *Amyotroph. Lateral. Scier.* 10(2): 99-106.
5. Phuphanich S, et al. (2005) Oral sodium phenylbutyrate in patients with recurrent malignant gliomas: a dose escalation and pharmacologic study. *Neuro. Oncol.* 7(2): 177-182.
6. Brahmachari S, Jana A, & Pahan K (2009) Sodium benzoate, a metabolite of cinnamon and a food additive, reduces microglial and astroglial inflammatory responses. *J. Immunol.* 183(9):5917-5927.
7. Camacho L H, et a. (2007) Phase I dose escalation clinical trial of phenylbutyrate sodium administered twice daily to patients with advanced solid tumors. *Invest. New Drugs* 25(2):131-138.
8. Wightman F & Lighty D C (1982) Identification of phenylacetic acid as a natural auxin in the shoots of higher plants. *physiol plant* 55:17-24.
9. Merzvinskyte R, Treigyte G, Savickiene J, Magnusson K E, & Navakauskiene R (2006) Effects of histone deacetylase inhibitors, sodium phenyl butyrate and vitamin B3, in combination with retinoic acid on granulocytic differentiation of human promyelocytic leukemia HL-60 cells. *Ann. N. Y. Acad. Sci.* 1091:356-367.

The invention claimed is:

1. A pharmaceutical composition for induction of activity to improve disease symptoms by regulating a gene expression using histone deacetylase inhibitors (HDAC) activity in multiple target cells comprising:
   a) a nuclear peroxisome proliferator-activated receptors PPAR, particularly PPARγ that improves symptoms of at least one of inflammation, pain, autoimmune diseases, neurodegenerative inflammatory diseases, cancer and diabetes type 2 to replace PPARγ agonists in the multiple target cells, b) the histone deacetylase inhibitors HDAC which possess anti-proliferative and anti-pain activity in a subject in need thereof, c) a synergistic combination of benzoate and phenylbutyrate and/or phenylacetate in association with a pharmaceutical carrier;

wherein the benzoate is present at a dosage of 10 to 250 mg/kg and phenylbutyrate and/or phenylacetate is present at a dosage of 0.1 to 1000 mg/kg.

2. The pharmaceutical composition of claim 1, wherein the pharmaceutical carrier is chosen from water, physiological saline, or another suitable solution.

3. The pharmaceutical composition of claim 2, wherein said induction of activity of the nuclear receptor PPARγ improves symptoms of at least one of inflammation, pain, autoimmune diseases, neurodegenerative inflammatory diseases, cancer and diabetes type 2 to replace PPARγ agonists.

4. The pharmaceutical composition of claim 3, wherein the inflammation is chosen from at least one: osteoarthritis, rheumatoid arthritis, atherosclerosis, periodontitis, hay fever; autoimmune diseases is chosen from Addison's disease, Agammaglobulinemia, Alopecia areata, Amyloidosis, Ankylosing spondylitis, Anti-GBM/Anti-TBM nephritis, Antiphospholipid syndrome (APS), Autoimmune hepatitis, Autoimmune inner ear disease (AIED), Axonal & neuronal neuropathy (AMAN), Behcet's disease, Bullous pemphigoid, Castleman disease (CD), Celiac disease, Chagas disease, Chronic inflammatory demyelinating polyneuropathy (CIDP), Chronic recurrent multifocal osteomyelitis (CRMO), Churg-Strauss, Cicatricial pemphigoid/benign mucosal pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Discoid lupus, Dressler's syndrome, Endometriosis, Eosinophilic esophagitis (EoE), Eosinophilic fasciitis, Erythema nodosum, Essential mixed cryoglobulinemia, Evans syndrome, Fibromyalgia, Fibrosing alveolitis, Giant cell arteritis (temporal arteritis), Giant cell myocarditis, Glomerulonephritis, Goodpasture's syndrome, Graves' disease, Guillain-Barre syndrome, Hashimoto's thyroiditis, Hemolytic anemia, Henoch-Schonlein purpura (HSP), Herpes gestationis or pemphigoid gestationis (PG), Hypogammalglobulinemia, Huntington disease, IgA Nephropathy, IgG4-related sclerosing disease, Inclusion body myositis (IBM), Interstitial cystitis (IC), Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus, Lupus P PAGE 318'ROVO AT 1/2312020 3:52:45 PM [Eastern Standard Time], SVR:W-PTOFAX-002115"DNIS:2738300'CSID: "ANI:5148454515"DURATION (fm.ss):02.05erythematous, Lyme disease chronic, Meniere's disease, Microscopic polyangiitis (MPA), Mixed connective tissue disease (MCTD), Mooren's ulcer, Mucha-Habermann disease, Multiple sclerosis (MS), Myasthenia gravis, Myositis, Narcolepsy, Neuromyelitis optica, Neutropenia, Ocular cicatricial pemphigoid, Optic neuritis, Palindromic rheumatism (PR), PANDAS (Pediatric Autoimmune Neuropsychiatric Disorders Associated with *Streptococcus*), Paraneoplastic cerebellar degeneration (PCD), Paroxysmal nocturnal hemoglobinuria (PNH), Parry Romberg syndrome, Pars planitis (peripheral uveitis), Parsonnage-Turner syndrome, Pemphigus, Peripheral neuropathy, Perivenous encephalomyelitis, Pernicious anemia (PA), POEMS syndrome (polyneuropathy, organomegaly, endocrinopathy, monoclonal gammopathy, skin changes), Polyarteritis nodosa, Polymyalgia rheumatic a, Polymyositis, Postmyocardial infarction syndrome, Postpericardiotomy syndrome, Primary biliary cirrhosis, Primary sclerosing cholangitis, Progesterone dermatitis, Psoriasis, Psoriatic arthritis, Pure red cell aplasia (PRCA), Pyoderma gangrenosum, Raynaud's phenomenon, Reactive Arthritis, Reflex sympathetic dystrophy, Reiter's syndrome, Relapsing polychondritis, Restless legs syndrome (RLS), Retroperitoneal fibrosis, Rheumatic fever, Rheumatoid arthritis (RA), Sarcoidosis, Schmidt syndrome, Scleritis, Scleroderma, Sjogren's syndrome, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis, Thrombocytopenic purpura (TTP), Tolosa-Hunt syndrome (THS), Transverse myelitis, Type 1 diabetes, Ulcerative colitis (UC), Undifferentiated connective tissue disease (UCTD), Uveitis, Vasculitis, Vitiligo, Wegener's granulomatosis (now termed Granulomatosis with Polyangiitis (GPA)); and neurodegenerative inflammatory diseases is chosen from Multiple Sclerosis, Parkinson disease, Alzheimer, ALS or Lou Gehrig's disease.

5. The pharmaceutical composition of claim 1 includes use of a physiological amount of benzoate substantially at the same time as a physiological amount of phenylbutyrate for inducing activity of a nuclear receptor PPARγ in a subject in need thereof, wherein benzoate and phenylbutyrate and/or phenylacetate are each in association with a pharmaceutical carrier.

6. The composition of claim 5, wherein said inducing activity of a nuclear receptor PPARγ improves symptoms of at least one of inflammation, pain, autoimmune diseases, neurodegenerative inflammatory diseases, cancer and diabetes type 2 to replace PPARγ agonists.

7. The composition of claim 6, wherein the inflammation is chosen from osteoarthritis, rheumatoid arthritis, atherosclerosis, periodontitis, hay fever; autoimmune diseases is chosen from Addison's disease, Agammaglobulinemia, Alopecia areata, Amyloidosis, Ankylosing spondylitis, Anti-GBM/Anti-TBM nephritis, Antiphospholipid syndrome (APS), Autoimmune hepatitis, Autoimmune inner ear disease (AIED), Axonal & neuronal neuropathy (AMAN), Behcet's disease, Bullous pemphigoid, Castleman disease (CD), Celiac disease, Chagas disease, Chronic inflammatory demyelinating polyneuropathy (CIDP), Chronic recurrent multifocal osteomyelitis (CRMO), Churg-Strauss, Cicatricial pemphigoid/benign mucosal pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Discoid lupus, Dressler's syndrome, Endometriosis, Eosinophilic esophagitis (EoE), Eosinophilic fasciitis, Erythema nodosum, Essential mixed cryoglobulinemia, Evans syndrome, Fibromyalgia, Fibrosing alveolitis, Giant cell arteritis (temporal arteritis), Giant cell myocarditis, Glomerulonephritis, Goodpasture's syndrome, Graves' disease, Guillain-Barre syndrome, Hashimoto's thyroiditis, Hemolytic anemia, Henoch-Schonlein purpura R 24-PAGE 518'RCVD AT 1/2312020 3:52:45 Pm [Eastern Stanldard Time], SVR:W-JPTOFAX-002115"DNIS: 2738300'Celo: AIII:514845451 6 DURATION (nmM-ss): 02.05 (HSP), Herpes gestationis or pemphigoid gestationis (PG), Hypogammalglobulinemia, Huntington disease, igA Nephropathy, IgG4-related sclerosing disease, inclusion body myositis (IBM), Interstitial cystitis (IC), Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus, Lupus erythematous, Lyme disease chronic, Meniere's disease, Microscopic polyangiitis (MPA), Mixed connective tissue disease (MCTD), Mooren's ulcer, Mucha-Habermann disease, Multiple sclerosis (MS), Myasthenia gravis, Myositis, Narcolepsy, Neuromyelitis optica, Neutropenia, Ocular cicatricial pemphigoid, Optic neuritis, Palindromic rheumatism (PR), PANDAS (Pediatric Autoimmune Neuropsychiatric Disorders Associated with *Streptococcus*), Paraneoplastic cerebellar degeneration (PCD), Paroxysmal nocturnal hemoglobinuria (PNH), Parry Romberg syndrome, Pars planitis (peripheral uveitis), Parsonnage-Turner syndrome, Pemphigus, Peripheral neuropathy, Perivenous encephalomyelitis, Pernicious anemia (PA), POEMS syndrome (polyneuropathy, organomegaly, endocrinopathy, monoclonal gammopathy, skin changes), Polyarteritis nodosa, Polymyalgia rheumatic a, Polymyositis, Postmyocardial infarction syndrome, Postpericardiotomy syndrome, Primary biliary cirrhosis, Primary sclerosing cholangitis, Progesterone dermatitis, Psoriasis, Psoriatic arthritis, Pure red cell aplasia (PRCA), Pyoderma gangrenosum, Raynaud's phenomenon, Reactive Arthritis, Reflex sympathetic dystrophy, Reiter's syndrome, Relapsing polychondritis, Restless legs syndrome (RLS), Retroperitoneal fibrosis, Rheumatic fever, Rheumatoid arthritis (RA), Sarcoidosis, Schmidt syndrome, Scleritis, Scleroderma, Sjogren's syndrome, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis, Thrombocytopenic purpura (TTP), Tolosa-Hunt syndrome (THS), Transverse myelitis, Type 1 diabetes, Ulcerative colitis (UC), Undifferentiated PAGE 6 18 RCVD AT 112312020 3:52:45 PM [Eastern Standard Time] x SVR:W PTOFAX-00215" DNIS:2738300—CSID: 'AI:5148454515" DURATION (mm-ss):02-0 5connective tissue disease (UCTD), Uveitis, Vasculitis, Vitiligo, Wegener's granulomatosis (now termed Granulomatosis with Polyangiitis (GPA)); and neurodegenerative inflammatory diseases is chosen from Multiple Sclerosis, Parkinson disease, Alzheimer, ALS or Lou Gehrig's disease.

\* \* \* \* \*